United States Patent
Ohishi

(10) Patent No.: US 11,793,478 B2
(45) Date of Patent: Oct. 24, 2023

(54) MEDICAL IMAGE PROCESSING APPARATUS, MEDICAL IMAGE PROCESSING METHOD, AND X-RAY DIAGNOSTIC APPARATUS

(71) Applicant: CANON MEDICAL SYSTEMS CORPORATION, Otawara (JP)

(72) Inventor: Satoru Ohishi, Otawara (JP)

(73) Assignee: CANON MEDICAL SYSTEMS CORPORATION, Otawra (JP)

(*) Notice: Subject to any disclaimer, the term of this patent is extended or adjusted under 35 U.S.C. 154(b) by 31 days.

(21) Appl. No.: 15/938,206

(22) Filed: Mar. 28, 2018

(65) Prior Publication Data

US 2018/0279983 A1  Oct. 4, 2018

(30) Foreign Application Priority Data

Mar. 28, 2017 (JP) ................ 2017-063713
Mar. 27, 2018 (JP) ................ 2018-060553

(51) Int. Cl.
*G06K 9/00* (2022.01)
*A61B 6/00* (2006.01)
(Continued)

(52) U.S. Cl.
CPC ............ *A61B 6/504* (2013.01); *A61B 6/481* (2013.01); *A61B 6/486* (2013.01); *G06T 7/0016* (2013.01);
(Continued)

(58) Field of Classification Search
CPC ... G06T 7/0012; G06T 7/0014; G06T 7/0016; G06T 7/20; G06T 7/254; G06T 7/30;
(Continued)

(56) References Cited

U.S. PATENT DOCUMENTS 4,335,427 A * 6/1982 Hunt ................ G06T 5/50
382/130
4,729,379 A * 3/1988 Ohe ................ G06T 5/50
348/E5.089

(Continued)

FOREIGN PATENT DOCUMENTS

CN 101023871 A 8/2007
JP 2007-215925 A 8/2007
(Continued)

OTHER PUBLICATIONS

Combined Chinese Office Action and Search Report dated Jun. 3, 2021 in Chinese Patent Application No. 201810264437.4 (with English translation of Categories of Cited Documents), 23 pages.
(Continued)

*Primary Examiner* — Eric Rush
(74) *Attorney, Agent, or Firm* — Oblon, McClelland, Maier & Neustadt, L.L.P.

(57) ABSTRACT

A medical image processing apparatus comprises processing circuitry configured to select a reference image from blood vessel images based on contrast images acquired in time series and conduct a transformation process on other blood vessel images such that blood vessel shapes in the other blood vessel images match a blood vessel shape in the reference image, generate a color image where a color that corresponds to a temporal change in a pixel value is assigned to each pixel based on the blood vessel images after the transformation process, and display the color image on a display.

20 Claims, 7 Drawing Sheets

(51) Int. Cl.
*G06T 7/00* (2017.01)
*G06T 7/33* (2017.01)

(52) U.S. Cl.
CPC .............. *G06T 7/337* (2017.01); *A61B 6/484* (2013.01); *A61B 6/5288* (2013.01); *A61B 6/541* (2013.01); *G06T 7/0014* (2013.01); *G06T 2207/10116* (2013.01); *G06T 2207/20224* (2013.01); *G06T 2207/30048* (2013.01); *G06T 2207/30101* (2013.01)

(58) Field of Classification Search
CPC .. G06T 7/32; G06T 7/337; G06T 7/38; G06T 2207/10076; G06T 2207/10081; G06T 2207/10116; G06T 2207/10121; G06T 2207/20221; G06T 2207/20224; G06T 2207/30004; G06T 2207/30048; G06T 2207/30101; G06T 2207/30104; G06T 2211/404; G06T 2211/412; G06K 2209/05; A61B 6/481; A61B 6/484; A61B 6/485; A61B 6/486; A61B 6/487; A61B 6/503; A61B 6/504; A61B 6/5288; A61B 6/541; A61B 8/06; A61B 8/065; A61B 8/481; A61B 8/5284
USPC ....... 382/100, 128, 130, 132, 162, 164, 165, 382/254, 276, 278, 294; 378/98.11, 378/98.12; 600/310, 312, 324, 329, 407, 600/419, 454, 458, 465, 467, 468, 504; 324/306

See application file for complete search history.

(56) References Cited

U.S. PATENT DOCUMENTS

| | | | | |
|---|---|---|---|---|
| 5,671,743 | A * | 9/1997 | Kawai ................. | A61B 6/504 600/431 |
| 7,941,000 | B2 * | 5/2011 | Rongen ............... | A61B 6/5235 382/128 |
| 8,463,012 | B2 * | 6/2013 | Rauch ................. | G06T 7/38 382/130 |
| 8,498,463 | B2 * | 7/2013 | Florent ............... | A61B 6/504 382/130 |
| 2006/0120581 | A1 * | 6/2006 | Eck ..................... | G06T 7/0016 382/128 |
| 2007/0195932 | A1 * | 8/2007 | Nakaura .............. | G06T 7/0016 378/98.12 |
| 2008/0019479 | A1 * | 1/2008 | Bernhardt ........... | G06T 3/4053 382/130 |
| 2009/0257631 | A1 * | 10/2009 | Baumgart ............ | G06T 5/50 382/128 |
| 2010/0004526 | A1 * | 1/2010 | Wei ..................... | C07D 473/04 382/130 |
| 2011/0305405 | A1 | 12/2011 | Kawamura | |
| 2011/0317881 | A1 * | 12/2011 | Bonnefous .......... | G06T 7/30 382/294 |
| 2012/0190967 | A1 * | 7/2012 | Nahm .................. | A61B 6/504 600/411 |
| 2012/0201439 | A1 * | 8/2012 | Rauch ................. | G06T 7/20 382/130 |
| 2013/0345559 | A1 * | 12/2013 | Haemmerich ...... | G06T 7/0016 600/431 |
| 2014/0334708 | A1 * | 11/2014 | Sakata ................ | G06T 7/0012 382/131 |
| 2015/0126862 | A1 * | 5/2015 | Pfister ................ | G06T 7/0016 600/431 |
| 2015/0150526 | A1 * | 6/2015 | Oh ...................... | A61B 6/504 382/132 |
| 2015/0161800 | A1 * | 6/2015 | Nagae ................. | A61B 6/504 382/122 |
| 2015/0335304 | A1 * | 11/2015 | Lavi .................... | G06T 7/0012 600/407 |
| 2016/0015348 | A1 * | 1/2016 | Ohishi ................ | A61B 6/504 600/431 |
| 2016/0051218 | A1 * | 2/2016 | Ohishi ................ | G06T 7/11 600/431 |
| 2016/0143605 | A1 * | 5/2016 | Nagae ................. | G06T 5/50 382/103 |
| 2016/0180525 | A1 * | 6/2016 | Reynolds ............ | G06T 7/0016 382/131 |
| 2018/0225825 | A1 * | 8/2018 | Baumgart ........... | G06T 7/0014 |
| 2019/0015061 | A1 * | 1/2019 | Liebeskind ......... | G06T 7/0012 |

FOREIGN PATENT DOCUMENTS

| | | |
|---|---|---|
| JP | 2009-297077 A | 12/2009 |
| JP | 2011-255060 | 12/2011 |
| JP | 2015-213536 | 12/2015 |
| JP | 2016-97077 | 5/2016 |

OTHER PUBLICATIONS

Chinese Office Action dated Jan. 13, 2022, issued in Chinese Patent Application No. 201810264437.4.

Japanese Office Action dated Jan. 4, 2022, issued in Japanese Patent Application No. 2018-060553.

* cited by examiner

MEDICAL IMAGE PROCESSING APPARATUS, MEDICAL IMAGE PROCESSING METHOD, AND X-RAY DIAGNOSTIC APPARATUS

CROSS-REFERENCE TO RELATED APPLICATIONS

This application is based upon and claims the benefit of priority from Japanese Patent Application No. 2017-63713, filed on Mar. 28, 2017 and Japanese Patent Application No. 2018-060553, filed on Mar. 27, 2018; the entire contents of which are incorporated herein by reference.

FIELD

Embodiments described herein relate generally to a medical image processing apparatus, a medical image processing method, and an X-ray diagnostic apparatus.

BACKGROUND

There are conventional cases where the technology called color parametric imaging for obtaining the image of a parameter regarding for example the flow time of a contrast agent is applied to X-ray diagnostic apparatuses. During color parametric imaging, for example, changes in a pixel value of any pixel in a DSA image are regarded as changes in the density of the contrast agent, and the time when a time-series change in the pixel value reaches a peak or a specific value is calculated as a flow time. Then, during color parametric imaging, color information is assigned to the calculated time so that it is presented as a color image or a color animation.

DETAILED DESCRIPTION

A medical image processing apparatus comprises processing circuitry. The processing circuitry is configured to select a reference image from blood vessel images based on contrast images acquired in time series and conduct a transformation process on other blood vessel images such that blood vessel shapes in the other blood vessel images match a blood vessel shape in the reference image. The processing circuitry is configured to generate a color image where a color that corresponds to a temporal change in a pixel value is assigned to each pixel based on the blood vessel images after the transformation process. And the processing circuitry is configured to display the color image or the color animation on a display.

The medical image processing apparatus, a medical image processing method, and an X-ray diagnostic apparatus according to an embodiment are explained below with reference to drawings. Here, the following embodiment is not a limitation. Furthermore, in principle, the details described in one embodiment are also applied to other embodiments.

Figure 1:
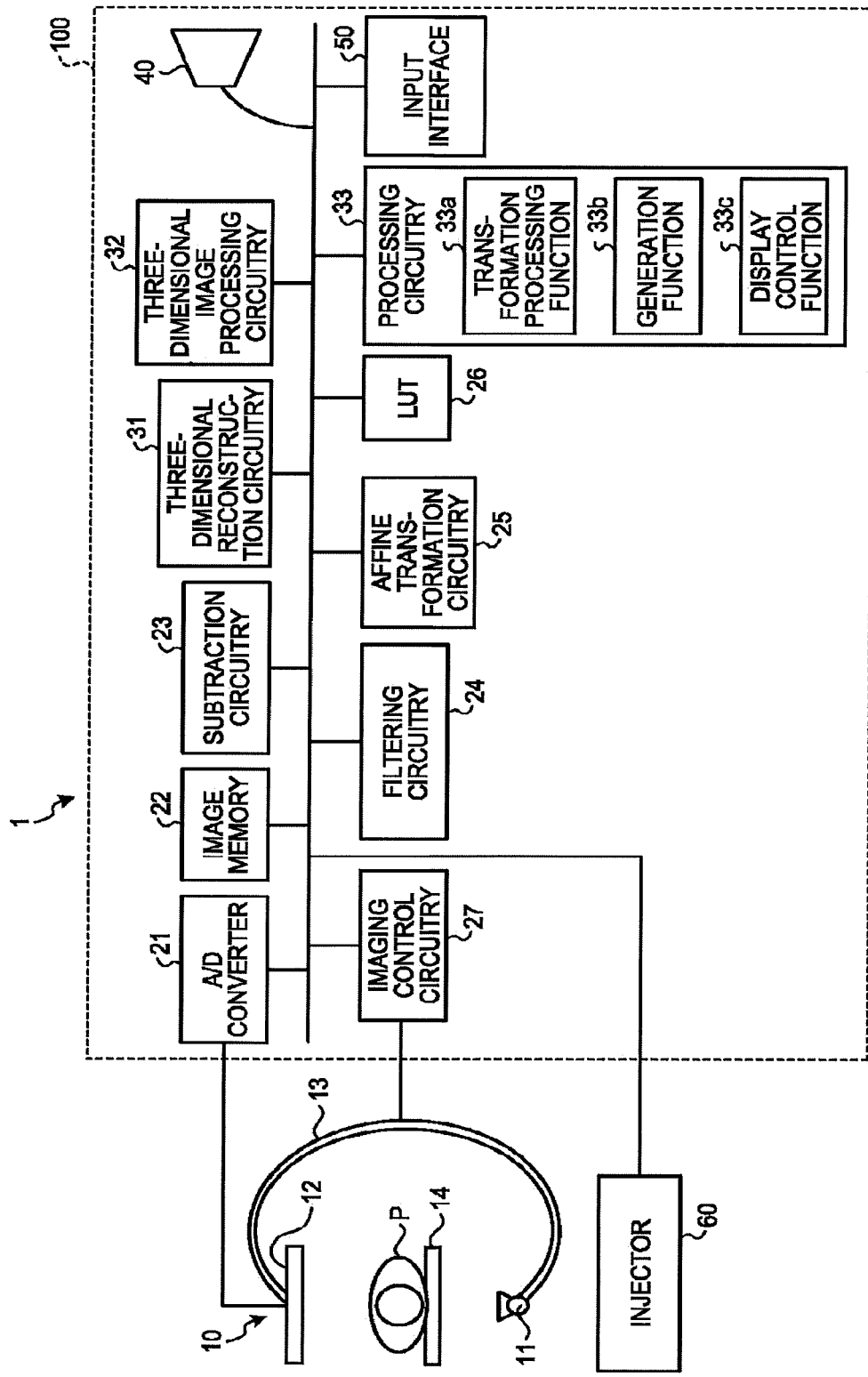
FIG. 1 is a block diagram that illustrates an example of the configuration of an X-ray diagnostic apparatus according to a first embodiment.

FIG. 1 is a diagram that illustrates an example of the configuration of an X-ray diagnostic apparatus 1 according to a first embodiment. As illustrated in FIG. 1, the X-ray diagnostic apparatus 1 according to the first embodiment includes an X-ray imaging mechanism 10 and a medical image processing apparatus 100. For example, the X-ray diagnostic apparatus 1 uses X-rays to acquire contrast images and, based on acquired contrast images, generates blood vessel images. According to the present embodiment, a subtraction image between a contrast image and a non-contrast image is explained as an example of blood vessel images.

The X-ray imaging mechanism 10 includes an X-ray tube 11, a detector (flat panel detector: FPD) 12, a C-arm 13, and a tabletop 14, and it is connected to an injector 60.

The injector 60 is a device for injecting a contrast agent through a catheter that is inserted into a subject P. Here, there may be cases in which injection of the contrast agent from the injector 60 is started in accordance with an injection start command that is received via the medical image processing apparatus 100 that is described later or in accordance with an injection start command that is directly input to the injector 60 by an operator such as technologists. Or there may be cases in which injection of contrast agent is performed manually by physicians via syringes.

The C-arm 13 holds the X-ray tube 11 and the detector 12 that detects X-rays irradiated from the X-ray tube 11. The C-arm 13 is rotated by an undepicted motor at a high speed like a propeller around the subject P that lies on the tabletop 14. Here, the C-arm 13 is held such that it is rotatable with regard to the XYZ axes that are the three axes that run at right angles, and it is individually rotated by undepicted driving circuitry with respect to each axis.

The X-ray tube 11 is an X-ray source that generates X-rays by using a high voltage that is supplied from an undepicted high-voltage generator. The detector 12 is a device where X-ray detecting elements for detecting X-rays transmitted through the subject P are arranged in a matrix. Each of the X-ray detecting elements included in the detector 12 outputs X-rays transmitted through the subject P to an A/D converter 21 that is described later.

As illustrated in FIG. 1, the medical image processing apparatus 100 includes an A/D (analog/digital) converter 21, an image memory 22, subtraction circuitry 23, filtering circuitry 24, affine transformation circuitry 25, a LUT (look up table) 26, imaging control circuitry 27, three-dimensional reconstruction circuitry 31, three-dimensional image processing circuitry 32, processing circuitry 33, a monitor 40, and an input interface 50. Here, the subtraction circuitry 23 is an example of the processing circuitry.

The monitor 40 displays various images that are processed by the medical image processing apparatus 100 and various types of information, such as a GUI (graphical user interface). For example, the monitor 40 is a CRT (cathode ray tube) monitor or a liquid crystal monitor.

The input interface 50 is equivalent to an input device such as mouse, keyboard, button, panel switch, touch command screen, foot switch, trackball, or joystick. The input interface 50 receives various commands from an operator and appropriately transfer received various commands to each circuitry in the medical image processing apparatus 100.

Furthermore, the input interface 50 includes, for example, an X-ray trigger button to give a command so as to irradiate X-rays. When the X-ray trigger button is pressed by an operator, the X-ray diagnostic apparatus 1 starts to acquire X-ray images.

The A/D converter 21 is connected to the detector 12, and it converts analog signals input from the detector 12 into digital signals and stores the converted digital signals as X-ray acquisition images in the image memory 22.

The image memory 22 stores X-ray acquisition images (projection data). Furthermore, the image memory 22 stores reconstruction data (volume data) that is reconstructed by the three-dimensional reconstruction circuitry 31 that is described later and three-dimensional images that are generated by the three-dimensional image processing circuitry 32. Furthermore, the image memory 22 may store programs executable by a computer.

The subtraction circuitry 23 generates subtraction images such as DSA (digital subtraction angiography) images. For example, the subtraction circuitry 23 generates subtraction images between acquisition images generated from X-ray signals that are acquired by imaging the subject without any contrast agent and acquisition images generated from X-ray signals that are acquired by imaging the subject with a contrast agent. More specifically, the subtraction circuitry 23 generates DSA images by using projection data on mask images (acquisition images generated from X-ray signals that are acquired by imaging the subject without any contrast agent) and contrast images (acquisition images generated from X-ray signals that are acquired by imaging the subject with a contrast agent), stored in the image memory 22 and acquired in substantially the same direction.

The filtering circuitry 24 conducts image processing filtering such as high-pass filtering, low-pass filtering, or the like. The affine transformation circuitry 25 scales up or down an image and moves the image, or the like. The LUT 26 performs a tone conversion.

The imaging control circuitry 27 controls various types of processes regarding imaging by the X-ray imaging mechanism 10 under the control of the processing circuitry 33 that is described later. For example, the imaging control circuitry 27 controls rotational imaging for taking X-ray images at a predetermined frame rate while the C-arm 13 is rotated. For instance, the imaging control circuitry 27 controls multiple rotational imagings after a single contrast agent is injected by using, as a trigger, the signal that is output when the injection of the contrast agent from the injector 60 is started. Here, the imaging control circuitry 27 controls the start of rotational imagings on the basis of the time elapsing from the start time of injection of a single contrast agent, thereby conducting rotational imaging in synchronized timing with the time when the contrast agent reaches the target for each rotational imaging. Furthermore, the imaging control circuitry 27 controls imaging for acquiring projection data at a predetermined frame rate without rotating the C-arm 13.

Furthermore, while the C-arm 13 is controlled so as to rotate, the imaging control circuitry 27 controls an undepicted high-voltage generator so as to cause the X-ray tube 11 to generate X-rays continuously or intermittently and controls the detector 12 so as to detect X-rays that are transmitted through the subject P. Here, the imaging control circuitry 27 causes the X-ray tube 11 to generate X-rays in accordance with an X-ray generation condition that is set by the processing circuitry 33, described later, for each rotational imaging.

The three-dimensional reconstruction circuitry 31 reconstructs reconstruction data (hereafter, referred to as three-dimensional image data or volume data) from projection data that is acquired by the X-ray imaging mechanism 10. For example, the three-dimensional reconstruction circuitry 31 reconstructs volume data from projection data that is composed of subtraction images after subtraction, stored in the image memory 22 after the subtraction circuitry 23 performs a subtraction on mask images and contrast images. Alternatively, the three-dimensional reconstruction circuitry 31 reconstructs volume data from projection data that is composed of mask images and contrast images stored in the image memory 22 after the A/D converter 21 performs a digital data conversion. Then, the three-dimensional reconstruction circuitry 31 stores reconstructed volume data in the image memory 22.

The three-dimensional image processing circuitry 32 generates three-dimensional medical image data from volume data that is stored in the image memory 22. For example, the three-dimensional image processing circuitry 32 generates volume rendering image data or MPR (Multi Planar Reconstruction) image data from volume data. Then, the three-dimensional image processing circuitry 32 stores generated three-dimensional image data in the image memory 22.

The processing circuitry 33 performs the overall control of the X-ray diagnostic apparatus 1. Here, the processing circuitry 33 is an example of the processing circuitry. Specifically, the processing circuitry 33 controls various operations related to imaging of X-ray images by the X-ray imaging mechanism 10, generation of displayed images, presentation of images displayed on the monitor 40, or the like. For example, the processing circuitry 33 causes the X-ray imaging mechanism 10 to conduct rotational imaging or causes the monitor 40 to display three-dimensional images generated from X-ray images that are taken during rotational imaging.

Furthermore, as illustrated in FIG. 1, the processing circuitry 33 performs a transformation processing function 33a, a generation function 33b, and a display control function 33c. Here, each of the processing functions performed by for example the transformation processing function 33a, the generation function 33b, and the display control function 33c, which are components of the processing circuitry 33 illustrated in FIG. 1, is stored in a storage device (e.g., the image memory 22) of the X-ray diagnostic apparatus 1 in a form of program executable by a computer. The processing circuitry 33 is a processor that reads each program from the storage device and executes it so as to perform the function that corresponds to each program. In other words, after each program has been read, the processing circuitry 33 has each function illustrated in the processing circuitry 33 of FIG. 1.

The image memory 22 is a semiconductor memory device such as a RAM (random access memory) or a flash memory or a storage device such as a hard disk or an optical disk, or the like. Furthermore, the subtraction circuitry 23, the filtering circuitry 24, the affine transformation circuitry 25, the LUT 26, the imaging control circuitry 27, the three-dimensional reconstruction circuitry 31, the three-dimensional image processing circuitry 32, and the processing circuitry 33 are electronic circuits such as CPUs (central processing units) or MPUs (micro processing units) or integrated circuits such as ASICs (application specific integrated circuit) or FPGAs (field programmable gate arrays).

An example of the configuration of the X-ray diagnostic apparatus 1 according to the first embodiment has been explained above. For example, a technology called parametric imaging for obtaining the image of a parameter regarding the flow time of a contrast agent is sometimes applied to the X-ray diagnostic apparatus 1 that is configured as described above. During parametric imaging, for example, a change in the pixel value at each position of a DSA image is regarded as a change in the density of a contrast agent, and the time when a change in the pixel value in time series reaches a peak or a specific value is calculated as a flow time. Furthermore, during parametric imaging, the color that corresponds to the calculated flow time is mapped to each position so that parametric-imaging image data (also referred to as "parametric image data") or parametric-imaging animation data is generated.

In conventional technologies, however, color parametric imaging cannot be applied as it is difficult to follow changes in the pixel value at each position of a DSA image with regard to a moving site such as abdominal blood vessels or the heart. Therefore, according to the first embodiment, the processing circuitry 33 performs the transformation processing function 33a, the generation function 33b, and the display control function 33c to apply color parametric imaging to moving sites such as the abdomen or the heart.

Figure 2:
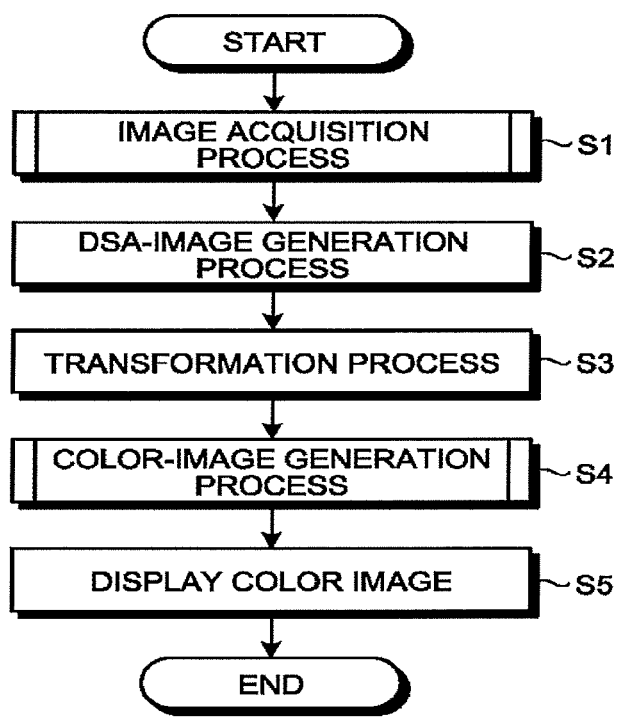
FIG. 2 is a flowchart that illustrates an example of the steps of a process performed by the X-ray diagnostic apparatus according to the first embodiment.

With reference to FIG. 2, an explanation is given below of an example of color parametric imaging by the X-ray diagnostic apparatus 1 according to the present embodiment. FIG. 2 is a flowchart that illustrates an example of the steps of a process performed by the X-ray diagnostic apparatus 1 according to the first embodiment. Here, in FIG. 2, an explanation is given of a case where the imaging targets are periodically moving blood vessels such as abdominal blood vessels or the heart. As illustrated in FIG. 2, the X-ray diagnostic apparatus 1 performs an image acquisition process (Step S1). For example, at Step S1, the X-ray diagnostic apparatus 1 receives the selection of an imaging program dedicated to parametric imaging from an operator via the input interface 50. More specifically, an operator selects an imaging program dedicated to parametric imaging for a moving object in the middle of angiographic or interventional procedures.

Figure 3:
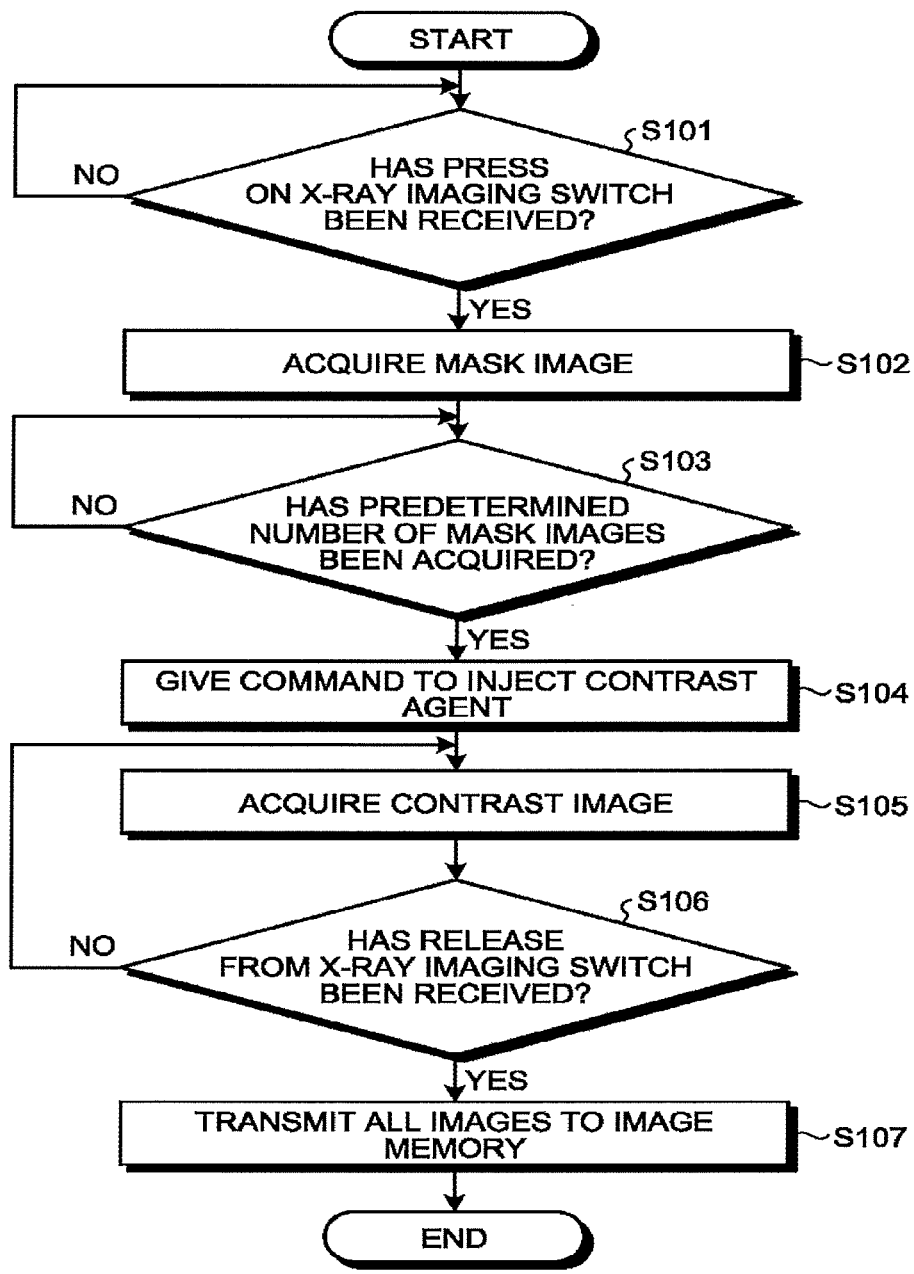
FIG. 3 is a flowchart that illustrates the steps of an image acquisition process by the X-ray diagnostic apparatus according to the first embodiment.

With reference to FIG. 3, the image acquisition process at Step S1 is explained. FIG. 3 is a flowchart that illustrates the steps of the image acquisition process by the X-ray diagnostic apparatus 1 according to the first embodiment. The image acquisition process illustrated in FIG. 3 corresponds to Step S1 of FIG. 2.

Step S101 illustrated in FIG. 3 is a step performed by the processing circuitry 33. At Step S101, the processing circuitry 33 determines whether press on the X-ray imaging switch has been received. Here, if it is not determined that press on the X-ray imaging switch has been received (Step S101, No), the processing circuitry 33 repeatedly performs a determination operation at Step S101. Conversely, if it is determined that press on the X-ray imaging switch has been received (Step S101, Yes), the processing circuitry 33 causes the imaging control circuitry 27 to perform Step S102. Here, it is preferable that a contrast agent is prepared in a syringe or injector 60 before the start of Step S101 so that the contrast agent is prepared to be injected.

Step S102 and Step S103 are steps that are performed by the imaging control circuitry 27. At Step S102, the imaging control circuitry 27 acquires mask images. For example, when the operator presses the X-ray imaging switch, the imaging control circuitry 27 controls the C-arm 13 so as to start to acquire mask images. Furthermore, the imaging control circuitry 27 repeatedly conducts imaging to acquire projection data in a certain period of time at a predetermined frame rate without rotating the C-arm 13. Here, the certain period of time is determined in accordance with the displacement time of an organ and an imaging interval. Specifically, approximately five seconds is one cycle for respiratory displacement, for example, and approximately one second is one cycle for displacement associated with heartbeats. Therefore, images are acquired during more than one cycle, typically two to three cycles.

At Step S103, the imaging control circuitry 27 determines whether a predetermined number of mask images has been acquired. The predetermined number may be previously set in the imaging program. Here, if it is not determined that the predetermined number of mask images has been acquired (Step S103, No), the imaging control circuitry 27 repeatedly performs a determination operation at Step S103. Conversely, if the imaging control circuitry 27 determines that the predetermined number of mask images has been acquired (Step S103, Yes), the processing circuitry 33 performs Step S104.

Step S104 is a step that is performed by the processing circuitry 33. At Step S104, the processing circuitry 33 gives a command to inject the contrast agent. For example, after the predetermined number of mask images has been acquired at Step S103, the processing circuitry 33 gives a command to an operator such as physicians so as to start to conduct imaging. This command may be given by displaying an icon indicating imaging on the monitor 40 or by using sounds. Alternatively, it is also possible to make a countdown for imaging start timing on the monitor 40. Then, physicians start to inject the contrast agent with a syringe after the timing is instructed.

Step S105 is a step that is performed by the imaging control circuitry 27. At Step S105, the imaging control circuitry 27 acquires contrast images. Here, the imaging control circuitry 27 controls imaging to acquire projection data at a predetermined frame rate without rotating the C-arm 13. The acquired contrast images are displayed on the monitor 40 by the processing circuitry 33 almost in real time.

Step S106 is a step that is performed by the processing circuitry 33. At Step S106, the processing circuitry 33 determines whether release from the X-ray imaging switch has been received. Here, if it is not determined that release from the X-ray imaging switch has been received (Step S106, No), the processing circuitry 33 proceeds to Step S105. Conversely, if it is determined that release from the X-ray imaging switch has been received (Step S106, Yes), the processing circuitry 33 terminates imaging and proceeds to Step S107. For example, an operator such as physicians observes the image displayed on the monitor 40 and releases the imaging switch after it is confirmed that the target site is significantly contrast-enhanced.

Step S107 is a step that is performed by the A/D converter 21. At Step S107, the A/D converter 21 transmits all the acquired images to the image memory 22. Furthermore, the A/D converter 21 may transmit X-ray images to the image memory 22 while X-ray images are acquired.

Figure 4:
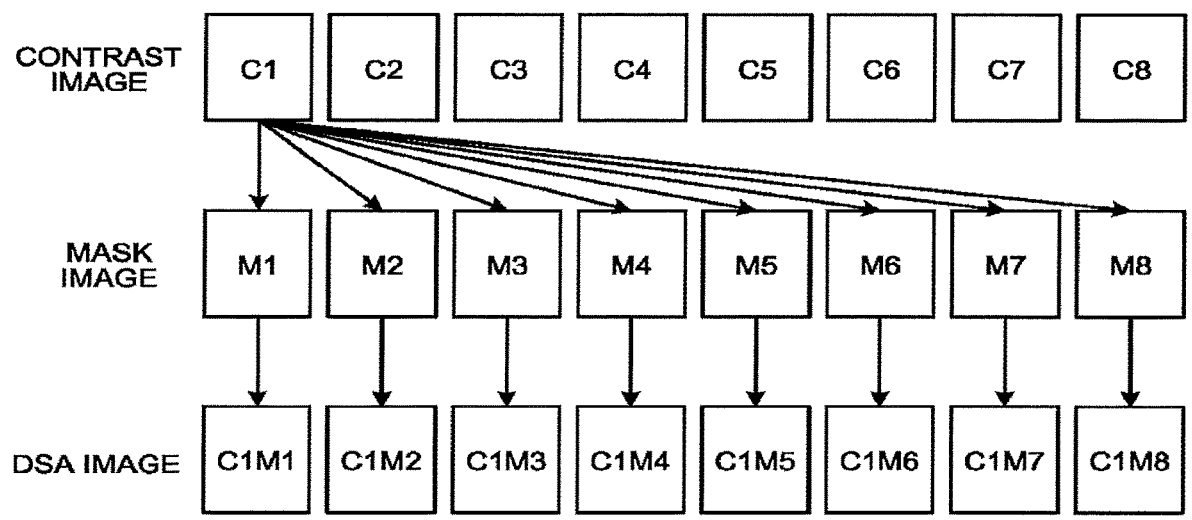
FIG. 4 is a diagram (1) that illustrates the first embodiment.

Reference is back to FIG. 2. Step S2 illustrated in FIG. 2 is a step that is performed by the subtraction circuitry 23. At Step S2, the subtraction circuitry 23 performs a DSA-image generation process. For example, the subtraction circuitry 23 reads mask images and contrast images, stored in the image memory 22, and conducts subtraction on the contrast images and the mask images to generate DSA images. Here, the subtraction circuitry 23 conducts subtraction on contrast images and mask images in all the phases and selects the optimum DSA images. FIG. 4 is a diagram that illustrates the first embodiment.

The upper section of FIG. 4 illustrates contrast images C1 to C8 that are acquired at Step S105 illustrated in FIG. 3, and the middle section of FIG. 4 illustrates mask images M1 to M8 that are acquired at Step S102. Here, the subtraction circuitry 23 conducts subtraction on, for example, the contrast image C1 and all the mask images M1 to M8 to generate respective DSA images C1M1 to C1M8. Then, the subtraction circuitry 23 performs image processing to determine the optimum DSA image for the contrast image C1 among the generated DSA images.

The image processing to determine the optimum DSA image is explained. With the X-ray diagnostic apparatus 1, a pixel on the path with high X-ray attenuation exhibits a low pixel value, and a pixel on the path with low X-ray attenuation exhibits a high pixel value. Furthermore, in DSA images, a pixel in the part where the pixel value decreases due to flow of the contrast agent exhibits a negative polarity (−). Here, if a structural object, such as organ or diaphragm, is moved due to body motion such as breathing between when to acquire a contrast image and when to acquire a mask image, a pixel in which an organ is overlapped in the contrast image and the mask image exhibits zero or an approximate value of zero in a DSA image in principle. Conversely, a pixel in which an organ is not overlapped in the contrast image and the mask image exhibits a positive polarity (+) or a negative polarity (−) in a DSA image.

Therefore, it may be determined that, in a DSA image, a pixel exhibiting a positive polarity (+) is a pixel where an organ or tissue is misaligned between when to acquire a contrast image and when to acquire a mask image. Thus, the subtraction circuitry 23 determines the DSA image that has the fewest number of pixels exhibiting a positive polarity (+) as the optimum DSA image for the contrast image C1 among the generated DSA images. In other words, the subtraction circuitry 23 subtracts a contrast image and a non-contrast image that has the fewest number of pixels having an opposite phase with respect to the pixel value at each position of a blood vessel image, thereby generating the blood vessel image. That is, a mask image and a contrast image in the identical phase are determined during image processing.

The subtraction circuitry 23 generates DSA images for all the acquired contrast images in the same manner. Specifically, each of the contrast images C2 to C8 is subtracted with regard to all the mask images M1 to M8, and the optimum DSA image is determined for each of the contrast images C2 to C8.

Reference is back to FIG. 2. Step S3 illustrated in FIG. 2 is a step that corresponds to the transformation processing function 33a. It is the step for implementing the transformation processing function 33a when the processing circuitry 33 reads and executes a predetermined program that corresponds to the transformation processing function 33a from the image memory 22. At Step S3, the transformation processing function 33a performs a transformation process. Here, the transformation processing function 33a is an example of a processer.

That is, the transformation processing function 33a selects a reference image from subtraction images that are generated by subtracting contrast images and non-contrast images acquired from a moving object in time series. For example, the transformation processing function 33a determines subtraction images in a phase with the least movement. Here, the transformation processing function 33a selects a reference image in accordance with a result of a correlation calculation between subtraction images. For example, the transformation processing function 33a performs a correlation calculation on subtraction images that are continuous in terms of time and selects an image with the largest number of highly correlated pixels as an image with the least movement.

Furthermore, with regard to subtraction images, the transformation processing function 33a uses the reference image as a reference and performs a transformation process on the other subtraction images. Specifically, with regard to subtraction images, the transformation processing function 33a performs a transformation process on the other subtraction images such that the position of a site in the subtraction images other than the reference image substantially matches the position of the site in the reference image. That is, the transformation processing function 33a selects a reference image from blood vessel images based on contrast images that have been acquired in time series and conducts a transformation process on the other blood vessel images such that blood vessel shapes in the other blood vessel images match the blood vessel shape in the reference image. For example, the transformation processing function 33a conducts a warping process on the other blood vessel images such that blood vessel shapes in the other blood vessel images match the blood vessel shape in the reference image. Here, the warping process is a process to adjust a position by partially transforming (warping) a site having a different form in DSA images during predetermined cycles on a pixel to pixel basis with respect to a reference image. More specifically, the transformation processing function 33a allocates a large number of areas of interest where a reference image locally matches a DSA image (also referred to as the target image to be processed) other than the reference image, and it calculates a motion vector on the basis of the area of interest. Then, the transformation processing function 33a calculates a motion vector on a pixel to pixel basis, for example, in accordance with the calculated motion vector and, based on it, transforms (warps) a predetermined site that is presented on the target image to be processed.

Here, for example, if the DSA image in the N-th phase is a reference image among the DSA images, the transformation processing function 33a performs a warping process on each of the subtraction images by using the N-th DSA image as a reference.

Figure 5:
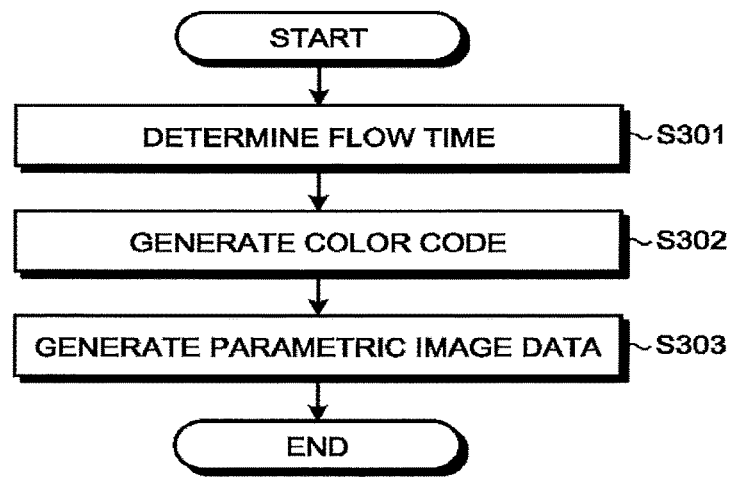
FIG. 5 is a flowchart that illustrates the steps of a color-image generation process by a generation function according to the first embodiment.

Step S4 illustrated in FIG. 2 is a step that corresponds to the generation function 33b. It is the step for implementing the generation function 33b when the processing circuitry 33 reads and executes a predetermined program that corresponds to the generation function 33b from the image memory 22. At Step S4, the generation function 33b performs a color-image generation process. Here, the generation function 33b is an example of a generator. For example, the generation function 33b generates a color image where the color that corresponds to a temporal change in a pixel value is assigned to each position of each subtraction image after the warping process. That is, the generation function 33b generates a color image where the color that corresponds to a temporal change in a pixel value is assigned to each pixel on the basis of blood vessel images after the transformation process. Here, the generation function 33b generates a color-parametric imaging image as the color image. With reference to FIG. 5, a color-image generation process is explained.

FIG. 5 is a flowchart that illustrates the steps of the color-image generation process by the generation function 33b according to the first embodiment. Here, the steps of the color-image generation process illustrated in FIG. 5 correspond to Step S4 illustrated in FIG. 2.

As illustrated in FIG. 5, the generation function 33b determines the flow time from the DSA image whose positional deviation due to the effect of motion has been corrected after the warping process (Step S301). Here, the flow time is a parameter that is defined on the basis of a time-series change in each pixel value where a change in the pixel value at each position of a DSA image is regarded as a change in the density of a contrast agent. The generation function 33b determines the flow time of the contrast agent injected into an object on the basis of a temporal change in the pixel value at each position of subtraction images. That is, the generation function 33b determines the flow time of a contrast agent injected into an object in accordance with a temporal change in the pixel value at each position of the blood vessel images after the transformation process. Furthermore, any method for calculating a flow time is selectable. For example, as the method for calculating a flow time, it is possible to select TTP (Time-to-Peak) that is a method for determining, as a flow time, the time when a time change in a pixel value becomes largest. Furthermore, for example, as the method for calculating a flow time, it is possible to select TTA (Time-to-Arrival) that is a method for determining, as a flow time, the time when a time change in a pixel value reaches a predetermined value or a predetermined percentage of the maximum value of a time change in a pixel value is reached.

Figure 6:
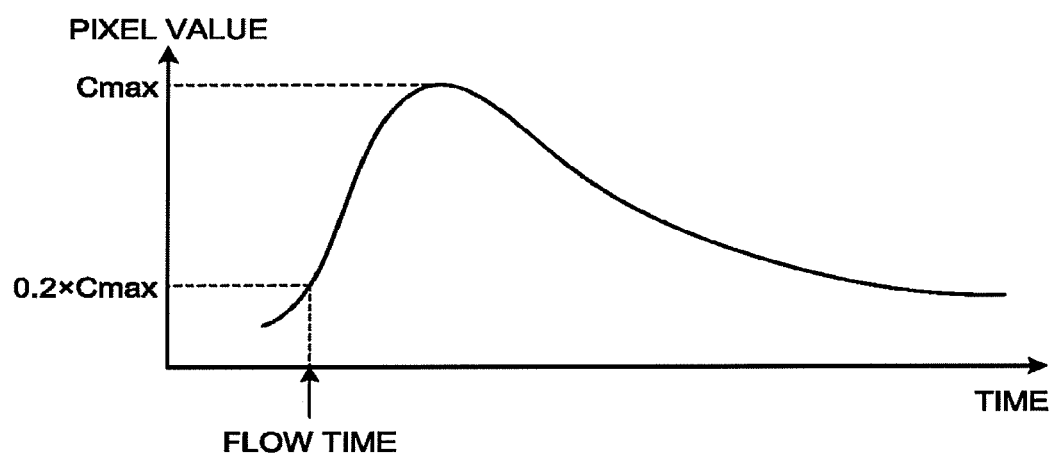
FIG. 6 is a diagram (2) that illustrates the first embodiment.

FIG. 6 is a diagram that illustrates the first embodiment. The horizontal axis in FIG. 6 indicates a time, and the vertical axis in FIG. 6 indicates a pixel value. The example of FIG. 6 illustrates a time density profile that is analyzed with respect to any pixel included in DSA images. Here, in FIG. 6, an explanation is given of a case where the method for determining a flow time is TTA.

As illustrated in FIG. 6, for example, the generation function 33b determines a flow time by analyzing a time density profile with respect to each pixel included in DSA images. In the example of FIG. 6, the generation function 33b determines that the time when 20% (0.2×Cmax) of the maximum pixel value (Cmax) is reached is a flow time.

Furthermore, the contents of FIG. 6 are only an example, and the example of FIG. 6 is not a limitation. For example, although the percentage for determining a flow time by using TTA is set to "20%" in the case illustrated in FIG. 6, this is not a limitation, and any percentage (or value) may be set. Furthermore, the method for determining a flow time may be not only TTA but also TTP.

Then, the generation function 33b generates a color code (Step S302). For example, if parametric image data is generated as a still image, the generation function 33b generates a single color code. Furthermore, if parametric image data is generated as an animation, the generation function 33b generates color codes that correspond to the number of frames included in an animation. A color-code generation process for still image generation and a color-code generation process for animation generation are sequentially explained below. Furthermore, although a default condition is previously set as the generation condition for generating a color code, it may be set appropriately by an operator.

Figure 7:
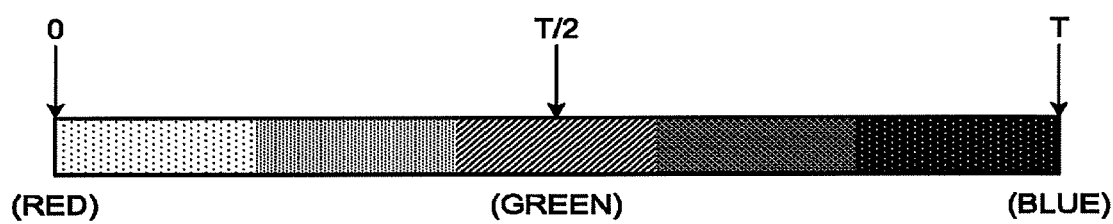
FIG. 7 is a diagram (3) that illustrates the first embodiment.

FIG. 7 is a diagram that illustrates the first embodiment. Here, in the case illustrated in FIG. 7, the method for determining a flow time is TTA. In TTA, the cycle and the initial value of a color code are set to "Auto" as default. Here, "Auto" indicates that automatic settings in accordance with an acquisition time period (imaging time period) of DSA images.

As illustrated in FIG. 7, for example, if the acquisition time period of DSA images is 0 to T seconds, the generation function 33b sets the cycle of a color code to "T" and the initial value of the color code to "0". This color code defines that "red" is set at "0" of flow time t, "red" gradually changes to "green" during "0" to "T/2", and "green" is set at "T/2". Furthermore, this color code defines that "green" gradually changes to "blue" during "T/2" to "T", and "blue" is set at "T".

In this way, the generation function 33b generates a color code for still images. Here, the contents of FIG. 7 are only an example, and the example of FIG. 7 is not a limitation. For example, although the method for determining a flow time is TTA in the case illustrated in FIG. 7, this is not a limitation, and it may be TTP. Furthermore, the order of colors defined in a color code in the example of FIG. 7 is not a limitation, and it may be set optionally. Furthermore, as it takes some time to initially flow a contrast agent, the initial value of the color code may be set to "D". The initial value "D" may be set by default, or it may be automatically determined from DSA images. According to a determining method, the time period in which more than a certain level of change first occurs in more than a certain range in DSA images may be set as "D".

Figure 8:
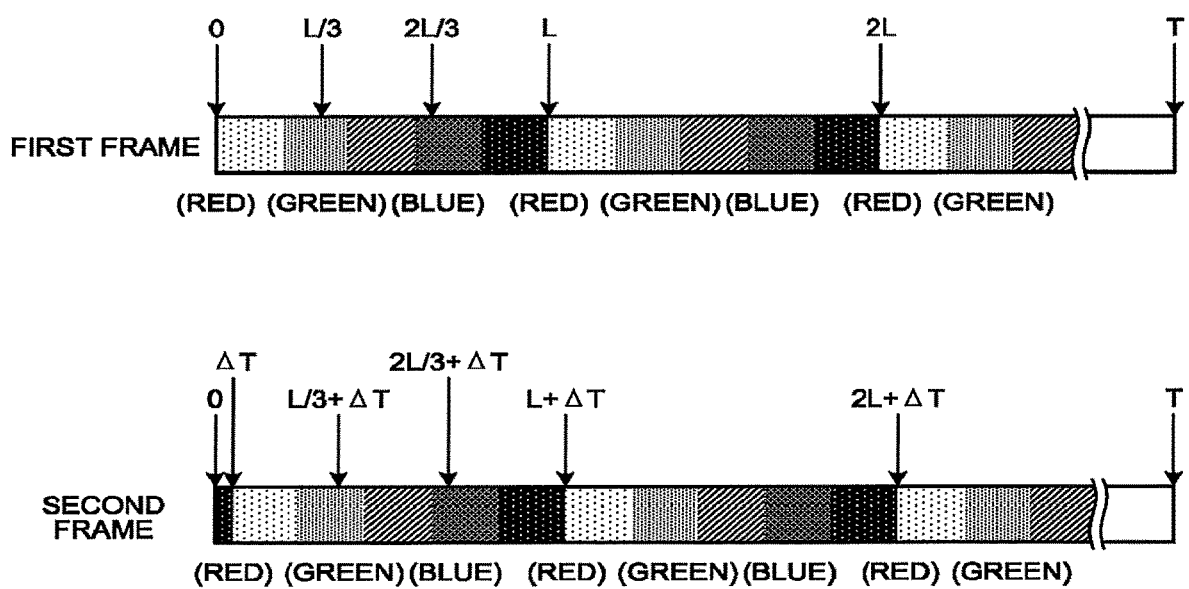
FIG. 8 is a diagram (4) that illustrates the first embodiment.

FIG. 8 is a diagram that illustrates the first embodiment. In the case illustrated in FIG. 8, the generation method for generating parametric image data as animation is CCC (Circular Color Coding). Furthermore, the method for determining a flow time in CCC may be TTA or TTP.

As illustrated in FIG. 8, for example, if the acquisition time period of DSA images is 0 to T seconds, the generation function 33b sets the cycle of a color code to "L(L<T)", the initial value of the color code to "0", and a step of the color code to "ΔT". Furthermore, the generation function 33b generates the number of color codes that corresponds to the number of frames included in an animation. For example, if the number of frames of an animation is "N=L/ΔT", where N is an integer, the generation function 33b generates N color codes for the first frame to the N-th frame.

For example, the color code of the first frame defines that "red" is set at "0" of the flow time t, "red" gradually changes to "green" during "0" to "L/3", and "green" is set at "L/3". Furthermore, the color code of the first frame defines that "green" gradually changes to "blue" during "L/3" to "2L/3" and "blue" is set at "2L/3". Furthermore, the color code of the first frame defines that "blue" gradually changes to "red" during "2L/3" to "L", and "red" is set again at "L". In this way, with the color code of the first frame, a change is made such that "red→green→blue→red" while the flow time t changes from "0" to "L". Furthermore, after "L", the color repeatedly changes from "L" to "2L". Specifically, with the color code of the first frame, a change is made such that "red→green→blue→red" while the flow time t changes from "L" to "2L". Furthermore, with the color code of the first frame, a change is made such that "red→green→blue→red" while the flow time t changes from "2L" to "3L". Afterward, in the same manner, with the color code of the first frame, a change is made such that "red→green→blue→red" until the flow time t reaches "T".

The color code of the second frame is generated by shifting the color code of the first frame by "ΔT". For example, the color code of the second frame defines that "red" is set at "Δt" of the flow time t, "red" gradually changes to "green" during "Δt" to "L/3+Δt", and "green" is set at "L/3+Δt". Furthermore, the color code of the second frame defines that "green" gradually changes to "blue" during "L/3+Δt" to "2L/3+Δt", and "blue" is set at "2L/3+Δt". Furthermore, the color code of the second frame defines that "blue" gradually changes to "red" during "2L/3+Δt" to "L+Δt", and "red" is set again at "L+Δt". Moreover, after "L+Δt", the color repeatedly changes from "L+ΔT" to "2L+ΔT" in the same manner as the color code of the first frame. Furthermore, before "ΔT", the color continuously changes from "0" to "ΔT".

That is, the color code of the N-th frame is generated by shifting the color code of the N−1th frame by "ΔT". In other words, the color code of the N-th frame is generated by shifting the color code of the first frame by "ΔT×(N−1)".

Here, the contents of FIG. 8 are only an example, and the example of FIG. 8 is not a limitation. For example, the order of colors defined in a color code is not limited to the example of FIG. 8, and it may be set optionally.

In this way, as color codes for an animation, the generation function 33b generates the number of color codes that correspond to the number of frames of the animation. It can be said that color codes for the animation are periodic color codes that define periodic changes in color in response to changes in a flow time. Furthermore, a processing condition for a parametric-image generation process is previously registered in an imaging program dedicated to parametric imaging. Here, the registered processing condition includes, for example, the method for determining a flow time, the cycle of a color code, the phase of a color code, the initial value of a color code, and information indicating whether it is a still image or an animation.

Reference is back to FIG. 5. The generation function 33b generates parametric image data (Step S303). For example, the generation function 33b assigns the color that corresponds to a temporal change in a pixel value to each pixel of DSA images, thereby generating parametric image data. That is, the generation function 33b assigns the color that corresponds to the flow time determined to each position so as to generate a color image.

Figure 9:
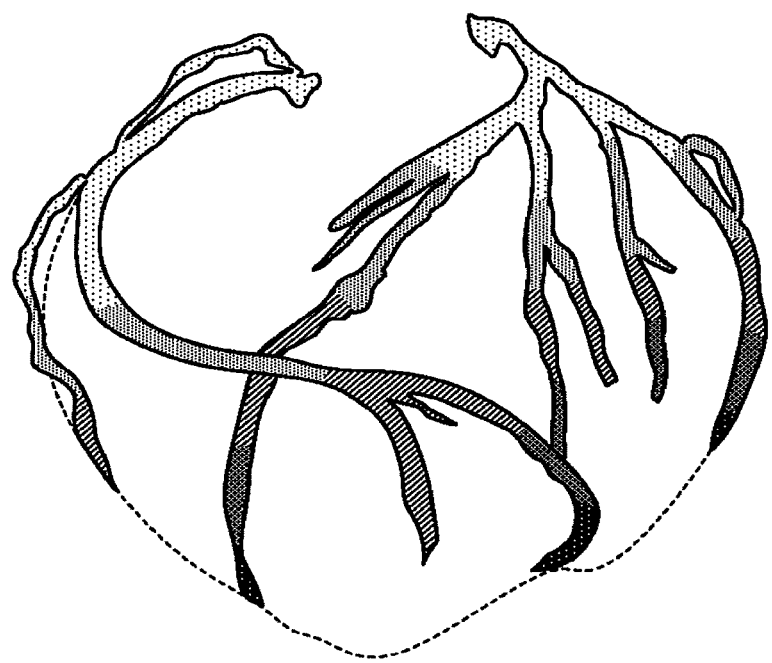
FIG. 9 is a diagram (5) that illustrates the first embodiment.

FIG. 9 is a diagram that illustrates the first embodiment. FIG. 9 illustrates parametric image data where blood vessels of the heart of the subject P are rendered.

As illustrated in FIG. 9, for example, the generation function 33b refers to the color code generated at Step S302 and assigns the color that corresponds to the flow time to each pixel so as to generate parametric image data.

Specifically, the generation function 33b generates parametric image data on still images. For example, the generation function 33b refers to the color code for a still image illustrated in FIG. 7 and assigns the color that corresponds to the flow time to each pixel so as to generate parametric image data.

Furthermore, the generation function 33b generates parametric image data on animation. For example, the generation function 33b refers to the color codes for an animation illustrated in FIG. 8 and generates the number of pieces of parametric image data that correspond to the number of frames included in the animation. Specifically, the generation function 33b assigns the color that corresponds to the flow time to each pixel on the basis of the color code of the first frame, thereby generating parametric image data on the first frame. Furthermore, the generation function 33b assigns the color that corresponds to the flow time to each pixel on the basis of the color code of the second frame, thereby generating parametric image data on the second frame. In this way, the generation function 33b assigns the color that corresponds to the flow time to each pixel on the basis of the color code of the N-th frame, thereby generating parametric image data on the N-th frame.

Although in the explanation of FIG. 9 the color is assigned in accordance with a flow time, it is preferable that luminance (brightness) is further adjusted in accordance with the maximum pixel value of each pixel. For example, it is preferable that the luminance of each pixel is a fraction "D/Dmax" of the maximum pixel value "D" of each pixel to the maximum pixel value "Dmax" in all the pixels included in DSA images.

In this way, the generation function 33b generates parametric image data on still images or animation. Then, the generation function 33b outputs the generated parametric image data to the display control function 33c.

Reference is back to FIG. 2. Step S5 illustrated in FIG. 2 is a step that corresponds to the display control function 33c. It is a step for implementing the display control function 33c when the processing circuitry 33 reads and executes a predetermined program that is equivalent to the display control function 33c from the image memory 22. At Step S5, the display control function 33c causes the monitor 40 to display a color image. Here, the display control function 33c is an example of a display controller. Here, the display control function 33c displays the color image as a still image. Alternatively, the display control function 33c displays the color images as an animation. After parametric image data on the N-th frame is displayed, the animation may be continuously displayed again, starting from the parametric image data on the first frame.

As described above, according to the first embodiment, the X-ray diagnostic apparatus 1 selects a reference image from subtraction images that are generated by subtracting contrast images and non-contrast images, which acquired from a moving object in time series, and with regard to the subtraction images, uses the reference image as a reference to perform a warping process on the other subtraction images. Then, the X-ray diagnostic apparatus 1 generates a color image by assigning the color that corresponds to a temporal change in a pixel value to each position in each subtraction image after the warping process. Then, the X-ray diagnostic apparatus 1 causes the monitor 40 to display the color image. Thus, according to the first embodiment, parametric imaging is applicable to moving objects.

In the explanation according to above-described first embodiment, to generate DSA images, the subtraction circuitry 23 determines a mask image and a contrast image that are in the identical phase during image processing; however, this is not a limitation on the embodiment. For example, the subtraction circuitry 23 may determine a non-contrast image that is in the phase identical to that of a contrast image on the basis of signals from a biosignal acquisition device and generate DSA images. In other words, the subtraction circuitry 23 generates a subtraction image by subtracting a contrast image and a non-contrast image that has the phase identical to that of a biological signal of the contrast image. Furthermore, in such a case, the X-ray diagnostic apparatus 1 is connected to a biosignal acquisition device that acquires biological signals from a periodically moving object. Here, the biosignal acquisition device may be, for example, a breath detection device that measures respiration phases. In such a case, the breath detection device includes a breath sensor, and it acquires respiratory waveforms of the subject P. Alternatively, the biosignal acquisition device may be, for example, cardiography equipment such as ECG (electrocardiogram)/EKG (elektrokardiogramm) which measures phases of the heart. Furthermore, although a biosignal acquisition device, such as a breath detection device or cardiography equipment, is an external device that is not a component of the X-ray diagnostic apparatus 1 in the explanation, it may be installed in the X-ray diagnostic apparatus 1 as a component of the X-ray diagnostic apparatus 1.

Furthermore, the subtraction circuitry 23 may determine a mask image whose phase is similar to that of a contrast image on the basis of signals from a biosignal acquisition device and perform image processing on the determined mask image and a mask image having a phase similar to that of the determined mask image together with the contrast image, thereby determining the optimum mask image.

Furthermore, in the case explained according to the above-described first embodiment, the transformation processing function 33a performs a correlation calculation to determine a reference image; however, this is not a limitation on the embodiment. For example, if the X-ray diagnostic apparatus 1 is connected to a biosignal acquisition device, the transformation processing function 33a may select a reference image on the basis of biological signals. Specifically, the transformation processing function 33a may select a reference image on the basis of biological signals from the blood vessel images based on contrast images acquired from a periodically moving object. Here, the transformation processing function 33a uses a time phase occurring with a desired repeatable nature in biological signals as a reference time phase and selects a DSA image in the reference time phase as a reference image. Furthermore, if there are multiple reference time phases in biological signals, a time phase with less movement is selected as a reference time phase from the existing reference time phases.

For example, the biosignal acquisition device acquires the heart phase as biological signals. Furthermore, the transformation processing function 33a selects a blood vessel image in a phase near mid-diastole based on the heart phase as a reference image. More specifically, the transformation processing function 33a determines a DSA image in mid-diastole, in which the heart phase is most stable, from EKG signals and selects the DSA image near mid-diastole as a reference image.

Alternatively, the biosignal acquisition device acquires a respiration phase as a biological signal. Furthermore, the transformation processing function 33a selects a blood vessel image in a phase near the maximum expiration based on the respiration phase as a reference image. More specifically, the transformation processing function 33a determines a DSA image with the maximum expiration, in which a respiratory waveform is most stable, and selects the DSA image near the maximum expiration as a reference image. That is, the transformation processing function 33a selects a reference image from subtraction images generated by subtracting a contrast image and a non-contrast image acquired from a periodically moving object, on the basis of biological signals.

The above-described embodiment is not a limitation on embodiments.

In the case explained according to the above-described embodiment, the imaging targets are periodically moving blood vessels such as abdominal blood vessels or the heart; however, this is not a limitation on embodiments. For example, the imaging targets do no move periodically. More specifically, the above-described color parametric imaging is applicable to a case where the imaging target is peristalsis of intestine, or the like. Furthermore, in such a case, the transformation processing function 33a uses a time phase occurring with a desired repeatable nature in peristalsis of intestine as a reference time phase and selects a DSA image in the reference time phase as a reference image. Furthermore, if there are multiple reference time phases in peristalsis of intestine, a time phase with less movement is selected as a reference time phase from the existing reference time phases.

Furthermore, in the explanation according to the above-described embodiment, an example of the blood vessel image is a subtraction image generated by the subtraction circuitry 23. However, this is not a limitation on embodiments. For example, instead of or in addition to the subtraction circuitry 23, the medical image processing apparatus 100 may include blood vessel image generation circuitry so that the blood vessel image generation circuitry generates blood vessel images based on contrast images. Here, the blood vessel image generation circuitry is an example of the processing circuitry.

For example, the blood vessel image generation circuitry may generate blood vessel images by using machine learning. For example, the blood vessel image generation circuitry first acquires multiple sets of learning data that has a combination of contrast images and subtraction images based on the contrast images and mask images. Then, the blood vessel image generation circuitry generates a learned model for removing background components (bones, soft tissues, or the like) other than blood vessels in contrast images through supervised learning that uses learning data with which a contrast image is input and a subtraction image is output. Then, the blood vessel image generation circuitry inputs multiple contrast images acquired in time series to the learned model. Thus, the blood vessel image generation circuitry generates blood vessel images by removing background components from contrast images.

According to another example, the blood vessel image generation circuitry performs low-pass filtering processing on contrast images so as to generate an image that corresponds to a low-frequency component (soft tissue, or the like) in each contrast image. Then, the blood vessel image generation circuitry subtracts contrast images and an image after the low-frequency processing, thereby removing low frequency components other than high-frequency components (blood vessels, or the like) from each contrast image. Thus, the blood vessel image generation circuitry removes background components from contrast images to generate blood vessel images. That is, the blood vessel image generation circuitry subtracts a contrast image and an image obtained by conducting low-frequency processing on a contrast image, thereby generating a blood vessel image.

Furthermore, high-frequency components in contrast images sometimes include edge components of organs or bones as well as blood vessels. Moreover, if a blood vessel image is generated by subtracting a contrast image including an edge component of organs or bones and an image obtained by conducting low-frequency processing on the contrast image, the edge component of the organs or bones sometimes remain in a blood vessel image. However, contrary to blood vessels (contrast agent components), edge components of bone tissues do not change in the direction of a temporal sequence. Therefore, even if edge components of organs or bones remain in blood vessel images, parametric imaging is less affected.

The term "processor" used in the above explanation means, for example, a CPU (central processing unit), a GPU (graphics processing unit), or a circuit, such as an application specific integrated circuit (ASIC), a programmable logic device (e.g., a simple programmable logic device (SPLD), a complex programmable logic device (CPLD), or a field programmable gate array (FPGA)). The processor reads a program stored in memory circuitry and executes it, thereby implementing the function. Furthermore, instead of storing programs in the memory circuitry, a configuration may be such that programs are directly installed in a circuit of a processor. In this case, the processor reads the program installed in the circuit and executes it, thereby implementing the function. Furthermore, with regard to each processor according to the present embodiment, each processor is not always configured as a single circuit but also configured as a single processor by combining multiple independent circuits so that its function is implemented. Furthermore, components in FIG. 1 may be integrated into a single processor to implement its function.

Furthermore, the contents illustrated in FIG. 1 are only an example. For example, although FIG. 1 illustrates the circuitry (processors) of the subtraction circuitry 23, the filtering circuitry 24, the affine transformation circuitry 25, the LUT 26, the imaging control circuitry 27, the three-dimensional reconstruction circuitry 31, the three-dimensional image processing circuitry 32, and the processing circuitry 33, these circuitries do not always need to be configured independently. For example, any circuitry included in the circuitry may be combined appropriately to be configured.

In explanation according to the above-described embodiment, components of each device illustrated are functionally conceptual and do not necessarily need to be physically configured as illustrated in the drawings. Specifically, specific forms of separation and combination of each device are not limited to those depicted in the drawings, and a configuration may be such that all or some of them are functionally or physically separated or combined in an arbitrary unit depending on various types of loads or usage. Furthermore, all or any of various processing functions performed by each device may be implemented by a CPU and a program analyzed and executed by the CPU or implemented as wired logic hardware.

Furthermore, the control method described in the above embodiment may be implemented if a prepared control program is performed by a computer such as a personal computer or workstation. The control program may be distributed via a network such as the Internet. Moreover, the control program may be stored in a recording medium readable by a computer, such as a hard disk, flexible disk (FD), CD-ROM, MO, or DVD, and may be executed by being read from a recording medium by a computer.

Furthermore, in the case explained above, the X-ray diagnostic apparatus 1 performs color parametric imaging that is described in the first embodiment and the modification of the first embodiment; however, this is not a limitation on embodiments. For example, an image processing device, which acquires contrast images and mask images from the X-ray diagnostic apparatus 1, or an image processing device, which acquires subtraction images from the X-ray diagnostic apparatus 1, may conduct color parametric imaging that is described in the first embodiment and the modification of the first embodiment.

According to at least one of the above-described embodiments, parametric imaging is applicable to moving objects.

With the medical image processing apparatus according to the embodiment, parametric imaging is applicable to moving objects.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured to
generate, from a time series of images of a blood vessel, a reference image from a contrast image of the blood vessel acquired in time series, wherein the reference image is acquired in a presence of a contrast agent,
conduct a transformation process on blood vessel images other than the reference image such that blood vessel shapes of the blood vessel in the blood vessel images other than the reference image match a blood vessel shape of the blood vessel in the reference image by warping the blood vessel shapes on a pixel by pixel basis with respect to the blood vessel shape in the reference image,
for each pixel of a plurality of pixels,
calculate a pixel value that is assigned to the pixel based on the transformed blood vessel images after the transformation process,
determine a parameter based on a temporal change of the calculated pixel value of the pixel based on the transformed blood vessel images after the transformation process, and
determine a color that corresponds to the parameter,
generate a color image by assigning colors to pixels of the color image such that the assigned colors to the pixels of the color image correspond to the determined colors for the determined parameters of the plurality of pixels based on the transformed blood vessel images after the transformation process, and
display the color image on a display, wherein the processing circuitry is configured to generate subtraction images by conducting subtraction on the contrast image and mask images, and
perform image processing to determine an optimum subtraction image for the contrast image among the generated subtraction images, wherein optimum subtraction images are determined for each of a set of contrast images corresponding to the blood vessel images other than the reference image.

2. The medical image processing apparatus according to claim 1, wherein, for each pixel of the plurality of pixels, the processing circuitry is configured to determine, as the parameter, a flow time of a contrast agent injected into an object in accordance with the temporal change of the calculated pixel value of the pixel based on the transformed blood vessel images and determine a color that corresponds to the flow time at the pixel.

3. The medical image processing apparatus according to claim 1, wherein the processing circuitry is configured to generate the reference image in accordance with a result of a correlation calculation between the contrast image of the blood vessel and the time series of images of the blood vessel other than the reference image.

4. The medical image processing apparatus according to claim 1, wherein the processing circuitry is configured to generate the reference image from the contrast image of the blood vessel in accordance with a biological signal based on contrast images of a periodically moving object, the biological signal being acquired from the periodically moving object by a biosignal acquisition device, which is connected to the medical image processing apparatus.

5. The medical image processing apparatus according to claim 4,
wherein the processing circuitry is configured to generate the reference image using as the contrast image of the blood vessel a blood vessel image in a phase near maximum expiration based on a respiration phase, the respiration phase being acquired by the biosignal acquisition device as the biological signal.

6. The medical image processing apparatus according to claim 4,
wherein the processing circuitry is configured to generate the reference image using as the contrast image of the blood vessel a blood vessel image in a phase near mid-diastole based on a heart phase, the heart phase being acquired by the biosignal acquisition device as the biological signal.

7. The medical image processing apparatus according to claim 4, wherein the processing circuitry is configured to generate the reference image by subtracting (1) the contrast image of the blood vessel and (2) a non-contrast image of the blood vessel in the time series that has an identical phase to the biological signal of the contrast image of the blood vessel.

8. The medical image processing apparatus according to claim 1, wherein the processing circuitry is configured to generate the reference image by subtracting (1) the contrast image of the blood vessel and (2) a non-contrast image of the blood vessel in the time series that has a fewest number of pixels having an opposite phase with respect to a pixel value at each position of the contrast image of the blood vessel.

9. The medical image processing apparatus according to claim 1, wherein the processing circuitry is configured to generate the reference image by subtracting (1) the contrast image of the blood vessel and (2) an image obtained by performing low-frequency processing on the contrast image of the blood vessel.

10. The medical image processing apparatus according to claim 1, wherein the processing circuitry is configured to display the color image as a still image.

11. The medical image processing apparatus according to claim 1, wherein the processing circuitry is configured to display the color image as an animation.

12. A medical image processing method comprising:
generating, from a time series of images of a blood vessel, a reference image from a contrast image of the blood vessel acquired in the time series, wherein the reference image is acquired in a presence of a contrast agent;
conducting a transformation process on blood vessel images other than the reference image such that blood vessel shapes of the blood vessel in the blood vessel images other than the reference image match a blood vessel shape in the reference image by warping the blood vessel shapes on a pixel by pixel basis with respect to the blood vessel shape in the reference image,
for each pixel of a plurality of pixels,
calculating a pixel value that is assigned to the pixel based on the transformed blood vessel images after the transformation process,
determining a parameter based on a temporal change of the calculated pixel value of the pixel based on the transformed blood vessel images after the transformation process, and
determining a color that corresponds to the parameter,
generating a color image by assigning colors to pixels of the color image such that the assigned colors to the pixels of the color image correspond to the determined colors for the determined parameters of the plurality of pixels based on the transformed blood vessel images after the transformation process, and
displaying the color image on a display, wherein the medical image processing method further comprises:
generating subtraction images by conducting subtraction on the contrast image and mask images; and
performing image processing to determine an optimum subtraction image for the contrast image among the generated subtraction images, wherein optimum subtraction images are determined for each of a set of contrast images corresponding to the blood vessel images other than the reference image.

13. The medical image processing method according to claim 12, further comprising, for each pixel of the plurality of pixels, determining, as the parameter, a flow time of a contrast agent injected into an object in accordance with the temporal change of the calculated pixel value of the pixel based on the transformed blood vessel images and determining a color that corresponds to the flow time at the pixel.

14. The medical image processing method according to claim 12, further comprising generating the reference image in accordance with a result of a correlation calculation between the contrast image of the blood vessel and the blood vessel images other than the reference image.

15. The medical image processing method according to claim 12, further comprising generating the reference image from the contrast image of the blood vessel in accordance with a biological signal that is acquired from a periodically moving object by a biosignal acquisition device.

16. The medical image processing method according to claim 15, further comprising generating the reference image by subtracting (1) the contrast image of the blood vessel and (2) a non-contrast image of the blood vessel in the time series that has an identical phase to the biological signal of the contrast image of the blood vessel.

17. The medical image processing method according to claim 12, further comprising generating the reference image by subtracting (1) the contrast image of the blood vessel and (2) a non-contrast image of the blood vessel in the time series that has a fewest number of pixels having an opposite phase with respect to a pixel value at each position of the contrast image of the blood vessel.

18. The medical image processing method according to claim 12, further comprising generating the reference image by subtracting (1) the contrast image of the blood vessel and (2) an image obtained by performing low-frequency processing on the contrast image of the blood vessel.

19. The medical image processing method according to claim 12, further comprising displaying the color image as a still image or an animation.

20. An X-ray diagnostic apparatus comprising processing circuitry configured to
generate, from a time series of images of a blood vessel, a reference image from a contrast image of the blood vessel acquired in the time series, wherein the reference image is acquired in a presence of a contrast agent,
conduct a transformation process on blood vessel images other than the reference image such that blood vessel shapes of the blood vessel in the blood vessel images other than the reference image match a blood vessel shape of the blood vessel in the reference image by warping the blood vessel shapes on a pixel by pixel basis with respect to the blood vessel shape in the reference image, for each pixel of a plurality of pixels,
- calculate a pixel value that is assigned to the pixel based on the transformed blood vessel images after the transformation process,
- determine a parameter based on a temporal change of the calculated pixel value of the pixel based on the transformed blood vessel images after the transformation process, and
- determine a color that corresponds to the parameter, generate a color image by assigning colors to pixels of the color image such that the assigned colors to the pixels of the color image correspond to the determined colors for the determined parameters of the plurality of pixels based on the transformed blood vessel images after the transformation process, and display the color image on a display, wherein the processing circuitry is configured to generate subtraction images by conducting subtraction on the contrast image and mask images, and perform image processing to determine an optimum subtraction image for the contrast image among the generated subtraction images, wherein optimum subtraction images are determined for each of a set of contrast images corresponding to the blood vessel images other than the reference image.

* * * * *